(12) United States Patent
Iwao et al.

(10) Patent No.: US 8,808,731 B2
(45) Date of Patent: Aug. 19, 2014

(54) ADHESIVE PHARMACEUTICAL PREPARATION CONTAINING BISOPROLOL

(75) Inventors: Yoshihiro Iwao, Osaka (JP); Katsuyuki Ookubo, Osaka (JP); Katsuhiro Okada, Osaka (JP); Kunihiro Minami, Fukushima (JP); Shuichiro Yuasa, Fukushima (JP)

(73) Assignees: Nitto Denko Corporation, Osaka (JP); Toa Eiyo Ltd., Tokyo (JP)

( * ) Notice: Subject to any disclaimer, the term of this patent is extended or adjusted under 35 U.S.C. 154(b) by 676 days.

(21) Appl. No.: 12/066,095

(22) PCT Filed: Sep. 7, 2006

(86) PCT No.: PCT/JP2006/317764
§ 371 (c)(1),
(2), (4) Date: Jun. 19, 2008

(87) PCT Pub. No.: WO2007/029781
PCT Pub. Date: Mar. 15, 2007

(65) Prior Publication Data
US 2009/0291126 A1    Nov. 26, 2009

(30) Foreign Application Priority Data

Sep. 9, 2005 (JP) .............................. P. 2005-262559
Aug. 31, 2006 (JO) .............................. P. 2006-235270

(51) Int. Cl.
A61K 9/70 (2006.01)
A61P 9/12 (2006.01)
A61K 31/135 (2006.01)

(52) U.S. Cl.
USPC ......................................... 424/449; 514/652

(58) Field of Classification Search
None
See application file for complete search history.

(56) References Cited

U.S. PATENT DOCUMENTS

| 5,149,719 A | 9/1992 | Ferber et al. |
| 5,508,038 A | 4/1996 | Wang et al. |
| 6,117,447 A * | 9/2000 | Nakano et al. ................ 424/448 |

(Continued)

FOREIGN PATENT DOCUMENTS

| CA | 2 583 340 A1 | 4/2006 |
| CO | 0821712 | 2/2008 |

(Continued)

OTHER PUBLICATIONS

JP 2003313122 English Translation.pdf, 2010.*

(Continued)

*Primary Examiner* — Susan Tran
*Assistant Examiner* — William Craigo
(74) *Attorney, Agent, or Firm* — Sughrue Mion, PLLC

(57) ABSTRACT

An adhesive pharmaceutical preparation which has a less irritation to the skin surface, keeps excellent stability of bisoprolol in the preparation, and allows continuous administration of a pharmacologically effective amount of bisoprolol into the living body, is provided. The adhesive preparation 10 comprises a support 1, an adhesive layer 2 laminated on one surface of the support 1. The adhesive layer 2 is characterized by containing bisoprolol, polyisobutylene, tackifier, and an organic liquid ingredient compatible to polyisobutylene and tackifier. Thus, an adhesive pharmaceutical preparation which has a good adhesiveness with less irritation to the skin and which gives almost no pain at peel-off or removal from the skin surface with leaving almost no paste, can be provided. In addition, bisoprolol is very stably maintained in the preparation and a pharmacologically effective amount of bisoprolol can be administered continuously into the living body through the skin surface.

12 Claims, 1 Drawing Sheet

(56) References Cited

U.S. PATENT DOCUMENTS

| | | | |
|---|---|---|---|
| 6,303,141 | B1 | 10/2001 | Fischer et al. |
| 6,486,147 | B2 | 11/2002 | Baldo et al. |
| 7,029,693 | B2 | 4/2006 | Hori |
| 7,250,546 | B2 | 7/2007 | Tsuruda |
| 2004/0142024 | A1 | 7/2004 | Chono et al. |
| 2006/0078604 | A1 | 4/2006 | Kanios et al. |
| 2006/0240086 | A1 | 10/2006 | Tateishi et al. |
| 2009/0012181 | A1 | 1/2009 | Amano et al. |
| 2009/0169603 | A1 | 7/2009 | Iwao et al. |
| 2009/0169604 | A1 | 7/2009 | Iwao et al. |
| 2009/0291126 | A1 | 11/2009 | Iwao et al. |
| 2010/0098747 | A1 | 4/2010 | Iwao et al. |
| 2010/0227932 | A1 | 9/2010 | Amano et al. |

FOREIGN PATENT DOCUMENTS

| | | | |
|---|---|---|---|
| EP | 1 188 436 | A2 | 3/2002 |
| EP | 1652508 | A1 * | 5/2006 |
| JP | 03-127727 | A | 5/1991 |
| JP | 4-55487 | A | 2/1992 |
| JP | 6-145626 | A | 5/1994 |
| JP | 7-330591 | A | 12/1995 |
| JP | 9-511987 | A | 12/1997 |
| JP | 10-152434 | A | 6/1998 |
| JP | 11-29496 | A | 2/1999 |
| JP | 11-502827 | A | 3/1999 |
| JP | 2002-38114 | A | 2/2002 |
| JP | 2002-080349 | A | 3/2002 |
| JP | 2002-187836 | A | 7/2002 |
| JP | 2003-313122 | A | 11/2003 |
| JP | 2003313122 | A * | 11/2003 |
| JP | 2004-502725 | A | 1/2004 |
| JP | 2004-244585 | A | 9/2004 |
| JP | 2005-23088 | A | 1/2005 |
| JP | 2006-76994 | A | 3/2006 |
| JP | 2006-225319 | A | 8/2006 |
| KR | 10-2008-0077404 | A | 8/2008 |
| KR | 10-1246400 | B1 | 3/2013 |
| MX | 2008003328 | A | 7/2008 |
| WO | 01/043729 | A1 | 6/2001 |
| WO | 02/03969 | A2 | 1/2002 |
| WO | 2005/011662 | A1 | 2/2005 |
| WO | WO 2005011662 | A1 * | 2/2005 |
| WO | 20051072716 | A1 | 8/2005 |
| WO | 2006/044206 | A3 | 4/2006 |
| WO | 2006/080199 | A1 | 8/2006 |
| WO | 2007/029781 | A1 | 3/2007 |
| WO | 2007/069661 | A1 | 6/2007 |

OTHER PUBLICATIONS

Choi, Kor.J.Chem.Eng., 9, 1992.*
Japanese Information Offer Form dated Apr. 15, 2009.
European Patent Office Communication dated Dec. 23, 2008.
VISANTEX PIB General Information, 2008.
Extended European Search Report dated Oct. 29, 2008.
Australian Office Action issued in Application No. 2006288260, dated Nov. 22, 2010.
Communication from the Chinese Patent Office (Decision on Rejection) in corresponding CN 200680033186.4 dated May 25, 2011.
Communication from the Mexican Patent Office in corresponding MX/a/2008/003328 dated Jun. 2, 2011.
Office Action, dated Feb. 27, 2013, issued by the Taiwan Intellectual Property Office in Taiwanese Patent Application No. 097108005, which corresponds to U.S. Appl. No. 12/528,194.
Office Action, dated Mar. 5, 2013, issued by the Japanese Patent Office in Japanese Patent Application No. 2008-057691, which corresponds to U.S. Appl. No. 12/528,194.
Office Action, dated Mar. 13, 2013, issued by the Korean Intellectual Property Office in Korean Patent Application No. 10-2008-7016978, which corresponds to U.S. Appl. No. 12/097,260.
Office Action, dated Mar. 18, 2013, issued by the Israel Patent Office in Israeli Patent Application No. 200378, which corresponds to U.S. Appl. No. 12/528,194.
Communication, dated Feb. 29, 2012, issued by the Republic of Colombia Superintendency of Industry and Commerce in corresponding Colombian Application No. PCT/08-21712.
Communication, dated Feb. 28, 2012, issued by the Japanese Patent Office in corresponding Japanese Application No. 2006-235270.
Office Action, dated Aug. 19, 2013, issued by the Japanese Patent Office in counterpart Japanese Application No. 2012-120476.
Office Action, dated Sep. 17, 2013, issued by the Korean Intellectual Property Office in Korean Application No. 10-2009-7018633, which corresponds to U.S. Appl. No. 12/528,194.
Hearing Notice, dated Jan. 31, 2014, issued by the Indian Patent Office in counterpart Indian Application No. 1166/CHENP/2008.
Final Office Action, issued by the US Patent Office in related U.S. Appl. No. 12/097,260 on Jul. 29, 2011.
Office Action issued on Sep. 8, 2011 in Chinese Patent Application No. 200680046916.4.
Japanese Office Action dated Dec. 13, 2011 issued by the Japanese Patent Office in Japanese Application No. 2006-328922.
Tan, Hock S. et al., "Pressure-sensitive adhesives for transdermal drug delivery systems," PSTT vol. 2, No. 2, Feb. 1999, pp. 60-69.
Non-Final Office Action, issued by the US Patent Office in U.S. Appl. No. 12/097,260 on Sep. 15, 2010.
Non-Final Office Action, issued by the US Patent Office in U.S. Appl. No. 12/097,260 on Feb. 18, 2011.
Non-Final Office Action, issued by the US Patent Office in related U.S. Appl. No. 12/097,260 on Dec. 16, 2011.
International Search Report (PCT/ISA/210), issued by the International Searching Authority in counterpart International Application No. PCT/JP2006/324874 on Mar. 20, 2007.
Office Action dated May 10, 2013 issued by the Canadian Intellectual Property Office in corresponding Canadian Patent Application No. 2,678,424.
Extended European Search Report dated Jun. 15, 2012 issued in counterpart European Patent Application No. 06834629.5.
Chinese Office Action issued Oct. 27, 2010 in Chinese application No. 200880007650.1.
Russian Office Action issued May 27, 2011 in Russian application No. 2009137122.
Chinese Office Action issued Jul. 22, 2011 in Chinese application No. 200880007650.1.
Chinese Office Action issued Nov. 2, 2011 in Chinese application No. 200880007650.1.
Israeli Office Action issued Sep. 27, 2011 in counterpart Israeli application No. 200378.
Chinese Office Action issued Mar. 28, 2012 in Chinese application No. 200880007650.1.
Australian Office Action issued May 10, 2012 in Australian application No. 2008221861.
Australian Office Action issued Sep. 25, 2012 in Australian application No. 2008221861.
Office Action issued Sep. 9, 2012 in Japanese application No. 2008-057691.
Colombian Office Action issued Aug. 14, 2012 in Colombian application No. 09-95795.
Taiwanese Office Action issued Sep. 24, 2012 in Taiwanese application No. 097108005.
International Search Report issued Apr. 15, 2008 in application No. PCT/JP2008/054022.
Final Office Action issued by the USPTO in U.S. Appl. No. 12/528,194 on Jul. 29, 2011.
Advisory Action issued by the USPTO in U.S. Appl. No. 12/528,194 on Nov. 18, 2011.
Non-Final Office Action issued by the USPTO in U.S. Appl. No. 12/528,194 on Dec. 20, 2011.
English-language translation of WO 2006080199 (of record, pub. Aug. 3, 2006), completed Aug. 2011, Schreiber Translations Inc., 41 pages total.
Final Office Action issued by the USPTO in U.S. Appl. No. 12/528,194 on Jul. 13, 2012.
Office Action issued on Nov. 10, 2011 in the corresponding Colombian Patent Application No. 08-21712.
Extended European Search Report issued Jun. 3, 2013, in related European Patent Application No. 08721442.5.

(56) References Cited

OTHER PUBLICATIONS

Extended European Search Report dated Jul. 22, 2011, issued in the corresponding European application No. 11003489.9.
Communication dated Sep. 28, 2012 issued by the State Intellectual Property Office of PR China in counterpart Chinese Patent Application No. 200680033186.4.
Communication issued Mar. 22, 2013, by the Indian Patent Office in related Application No. 1166/CHENP/2008.
Office Action issued on Feb. 7, 2012 in the corresponding Taiwanese Patent Application No. 095133239.
Office Action issued on Mar. 5, 2012 in the corresponding Canadian Patent Application No. 2,621,867.
Communication dated Nov. 26, 2012 from the Colombian Superintendency of Industry and Commerce in counterpart Colombian application No. PCT/08-021712.
Communication dated Jan. 28, 2012 from the European Patent Office in counterpart European application No. 11003489.9.
Canadian Office Action dated Jul. 3, 2012 issued in Canadian Patent Application No. 2633125.
Taiwanese Office Action dated Jul. 27, 2012 issued in counterpart Taiwanese Patent Application No. 095133239.
Korean Office Action dated Jul. 10, 2012 issued in counterpart Korean Patent Application No. 10-2008-7005702.
Office Action, dated Jun. 19, 2013, issued by the Mexican Patent Office in counterpart Mexican Application No. MX/a/2009/008933.
Communication, dated Oct. 5, 2011, issued by the Japanese Patent Office in corresponding Japanese Application No. 2006-235270.
Communication issued Mar. 13, 2014 from the Korean Intellectual Property Office in a Korean application No. 10-2009-7018633, which corresponds to U.S. Appl. No. 12/528,194.

* cited by examiner

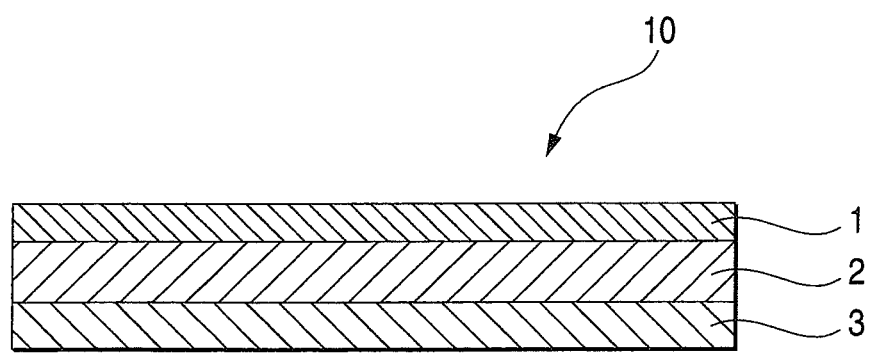

ADHESIVE PHARMACEUTICAL PREPARATION CONTAINING BISOPROLOL

TECHNICAL FIELD

The present invention relates to an adhesive pharmaceutical preparation containing bisoprolol for making continuously absorb bisoprolol into the body through the skin surface.

BACKGROUND ART

Bisoprolol which is a highly selective $\beta_1$-receptor antagonist in the sympathetic nerve has been used in amelioration of essential hypertension, angina pectoris, and arrhythmia, and its fumarate has been used as tablets for oral administration.

On the other hand, as a pharmaceutical preparation for treatment or prevention of diseases by administering a drug to the living body, a percutaneously absorbing preparation has attracted a great deal of attention in recent years, since drug metabolism by an initial effect passing through the liver and a variety of side effects can be avoided and the drug can be administered over a long period of time. Among them, a percutaneously absorbing adhesive preparation, in which an adhesive layer containing a drug is stuck on a skin surface, has been increasingly developed, since an operation of administration is easy and a dose can be strictly controlled. Such an adhesive preparation is required as it characteristic to have a releasability of a drug from an adhesive layer (transdermal permeability), stability of the drug contained in an adhesive layer with a lapse of day (prevention of decrease of the content of drug), stickiness on the skin surface (adhesiveness), appropriate cohesiveness for leaving no paste on the skin surface (prevention of leaving the paste after peeling-off), lower irritation to the skin (safety), and so on; thus, it is necessary to develop an adhesive pharmaceutical preparation which satisfies the above-required characteristics according to the kind of drugs.

As for a percutaneously absorbing pharmaceutical preparation, Patent Document 1 discloses an adhesive preparation containing menthol methylthiomethyl ether in order to enhance transdermal permeation of a physiologically active substance, for example, bisoprolol. Patent Document 2 has reported that addition of a third ingredient polyvinylpyrrolidone to a mixture of a particular rubber and polyacrylic acid in an adhesive preparation is capable of increasing the solubility of a drug without any adverse effect on the delivery rate of the drug, wherein the drug is exemplified by bisoprolol. In these patent documents, however, only bisoprolol has been exemplified as a drug, and no consideration has been made substantially on an adhesive preparation aimed to administer bisoprolol because an examination of the mutual interaction of bisoprolol with an adhesive itself has been done insufficiently. In addition, Patent Document 3 has proposed a percutaneously absorbing adhesive pharmaceutical preparation comprising bisoprolol in an acryl-type adhesive. In this preparation, however, it is difficult to say that stability of the drug and skin irritation caused by the drug have been investigated sufficiently, leaving room for improvement.

Patent Document 1: JP-A-11-29496
Patent Document 2: JP-T-09-511987
Patent Document 3: JP-A-2003-313122

DISCLOSURE OF THE INVENTION

Problems to be Solved by the Invention

The present invention has been achieved in view of such an actual situation; the purpose of the invention for solving the problems is to provide an adhesive pharmaceutical preparation which has a less irritation to the skin surface, keeps excellent stability of bisoprolol in the preparation, and allows continuous administration of a therapeutically or prophylactically effective amount of bisoprolol into the living body.

Means for Solving the Problems

The present inventors worked assiduously to solve the above problems, and found that an adhesive preparation suitable for administration of bisoprolol can be obtained by constituting a composition containing a certain ingredient in the adhesive layer of the preparation. The invention was thus completed.

That is, the invention is as follows.

1. An adhesive pharmaceutical preparation containing bisoprolol, which comprises a support and an adhesive layer on one side of the support, wherein the adhesive layer contains bisoprolol, polyisobutylene, a tackifier, and an organic liquid ingredient compatible with polyisobutylene and the tackifier.

2. The adhesive pharmaceutical preparation containing bisoprolol as described in the above item 1, wherein the content of bisoprolol per adhesive area of the adhesive preparation is 0.1 to 1 mg/cm$^2$.

3. The adhesive pharmaceutical preparation containing bisoprolol as described in the above item 1, wherein the content of bisoprolol per the total weight of the adhesive layer is 0.5 to 5% by weight.

4. The adhesive pharmaceutical preparation containing bisoprolol as described in any one of the above items 1 to 3, wherein the content of the organic liquid ingredient per the total weight of the adhesive layer is 20 to 40% by weight.

5. The adhesive pharmaceutical preparation containing bisoprolol as described in any one of the above items 1 to 4, which contains a fatty acid alkyl ester as the organic liquid ingredient.

6. The adhesive pharmaceutical preparation containing bisoprolol as described in any one of the above items 1 to 4, which contains a fatty acid alkyl ester and a long chain alcohol as the organic liquid ingredient.

7. The adhesive pharmaceutical preparation containing bisoprolol as described in the above item 6, wherein the compounding ratio by weight of the fatty acid alkyl ester (A) to the long chain alcohol (B) is 1:0 to 1:0.5 (A:B).

8. The adhesive pharmaceutical preparation containing bisoprolol as described in any one of the above items 5 to 7, wherein the fatty acid alkyl ester is isopropyl myristate.

9. The adhesive pharmaceutical preparation containing bisoprolol as described in any one of the above items 1 to 8, wherein the polyisobutylene contains two or more kinds of polyisobutylenes different in the molecular weight.

10. The adhesive pharmaceutical preparation containing bisoprolol as described in any one of the above items 1 to 9, wherein the polyisobutylene comprises a first polyisobutylene and a second polyisobutylene having a lower molecular weight than the first polyisobutylene.

11. The adhesive pharmaceutical preparation containing bisoprolol as described in the above item 10, wherein the viscosity average molecular weight of the first polyisobutylene is 1,800,000-5,500,000, and the viscosity average molecular weight of the second polyisobutylene is 40,000-85,000.

12. The adhesive pharmaceutical preparation containing bisoprolol as described in the above item 10 or 11, wherein the compounding ratio by weight of the first polyisobutylene (C) to the second polyisobutylene (D) is 1:0.1 to 1:3 (C:D).

13. The adhesive pharmaceutical preparation containing bisoprolol as described in any one of the above items 1 to 12, wherein the tackifier is an alicyclic saturated hydrocarbon resin.

14. The adhesive pharmaceutical preparation containing bisoprolol as described in any one of the above items 1 to 13, wherein the softening point of the tackifier is 90-150° C.

15. The adhesive pharmaceutical preparation containing bisoprolol as described in any one of the above items 1 to 14, wherein the content of tackifier per the total weight of the adhesive layer is 15 to 55% by weight.

In this invention, the content of the respective ingredients constituting the adhesive layer is properly adjusted so that the total amount becomes 100% by weight. In this connection, the exemplifications as described herein are not intended to limit the invention.

Advantage of the Invention

According to the invention, an adhesive pharmaceutical preparation which has a good adhesiveness with less irritation to the skin and which gives almost no pain at peel-off or removal from the skin surface with leaving almost no paste, can be provided. According to the adhesive preparation of the invention, bisoprolol is very stably maintained in the preparation and a therapeutically or prophylactically effective amount of bisoprolol can be administered continuously into the living body through the skin surface.

BRIEF DESCRIPTION OF DRAWINGS

FIG. 1 shows a cross section showing a mode for carrying out the invention on the bisoprolol-containing adhesive preparations.

EXPLANATION OF NUMERALS

1. Support; 2. Adhesive layer; 3. Peel-off liner; 10. Adhesive pharmaceutical preparation
Best Mode for Carrying Out the Invention Hereinafter, the invention will be explained in more detail along with a preferred mode for carrying out the invention. In "Description of Drawings", the same symbol is used for the same element to avoid the repetitive explanation. For the sake of convenience in illustration, the dimensions and ratio are not necessarily consistent with explanations.

FIG. 1 shows a cross section showing a mode for carrying out the invention on an adhesive pharmaceutical preparation containing bisoprolol (hereinafter referred simply to as "adhesive preparation"). The adhesive preparation 10 comprises a support 1, an adhesive layer 2 laminated on one surface of the support 1, and a peeling-off liner 3 laminated on the adhesive layer 2. The adhesive layer 2 is characterized by containing bisoprolol, polyisobutylene, tackifier, as well as an organic liquid ingredient compatible to polyisobutylene and tackifier.

Bisoprolol contained in the adhesive layer of the adhesive preparation has already been marketed as an oral preparation. In a case of tablets, it is contained in a form of acid addition salts such as bisoprolol fumarate. The bisoprolol used in the invention includes pharmaceutically acceptable salts in addition to a free form (free base) of bisoprolol. Therefore, it is desirous in the invention that bisoprolol in a free form with good transdermal permeability is contained in the adhesive layer since bisoprolol in a salt form is less transdermally permeable than the free form, though bisoprolol in a form of salts may be contained in the adhesive layer. Polyisobutylene contained in the adhesive layer favorably increases not only adhesiveness but also releasability of bisoprolol. In addition, the organic liquid ingredient contained favorably works to increase a transdermal permeability. Further, tackifier contained in the adhesive layer favorably increases the adhesiveness to the skin. Therefore, the adhesive preparation of the invention containing bisoprolol in the free form is favorable in releasability of bisoprolol, adhesiveness to the skin and a transdermal permeability because it contains a free-form of bisoprolol, polyisobutylene, tackifier and an organic liquid ingredient; thus, when the adhesive preparation is applied to the skin, in a preferred embodiment, it is possible that at least about 70% of bisoprolol contained in the preparation moves into the living body. Thus, the adhesive preparation of the invention is characterized in that it comprises a composition in which the availability of drug contained in the adhesive layer is very high.

The content of bisoprolol per the adhesive area in the preparation is preferably 0.1-1 $mg/cm^2$, more preferably 0.1-0.8 $mg/cm^2$, still more preferably 0.1-0.5 $mg/cm^2$. When the content of bisoprolol is less than 0.1 $mg/cm^2$, sometimes it is difficult to obtain a sufficient pharmacological effect; on the other hand, when the content is over 1 $mg/cm^2$, it is likely that skin irritation caused by the drug occurs.

The content of bisoprolol per the total amount of the adhesive layer is preferably 0.5-5% by weight, more preferably 0.5-4% by weight, still more preferably 0.5-3% by weight. When the content of bisoprolol is less than 0.5% by weight, it is likely that a sufficient pharmacological effect is hardly obtained. On the other hand, when it is over 5% by weight, bisoprolol sometimes exudes from the adhesive layer to form bleeding, which sometimes decreases the adhesiveness to the skin.

The organic liquid ingredient means a liquid organic one added in addition to a drug bisoprolol, and there is no limitation as far as it is compatible with polyisobutylene and tackifier. As the organic liquid ingredient, a fatty acid alkyl ester or a long-chain alcohol are preferably employed since it greatly contributes to enhance permeation of bisoprolol and improve solubility of bisoprolol in the adhesive layer. The organic liquid ingredient may be used alone or in combination of two or more species.

The fatty acid alkyl ester means, for example, those derived from a higher fatty acid of 12 to 16 carbon atoms, preferably 12 to 14 carbon atoms and a lower primary alcohol of 1 to 4 carbon atoms. The higher fatty acid includes, preferably, lauric acid (C12), myristic acid (C14), palmitic acid (C16), and more preferably myristic acid. The primary alcohol includes methyl alcohol, ethyl alcohol, propyl alcohol, isopropyl alcohol, butyl alcohol, and the like, and preferably isopropyl alcohol. Thus, the most preferred fatty acid alkyl ester is isopropyl myristate, which may used to attain enhancement of the absorption and improvement of the solubility of bisoprolol at high level.

The long-chain alcohol includes saturated or unsaturated alcohols of 12 to 28 carbon atoms, preferably 12 to 24 carbon atoms. As a long-chain alcohol, a saturated alcohol is preferably used in view of preservation stability. In addition, as a long-chain alcohol, straight or branched chain alcohols is exemplified, and they may be used as a mixture. The straight chain alcohol includes 1-dodecanol, 1-tetradecanol, 1-hexadecanol, stearyl alcohol, and the like, and in particular 1-dodecanol is preferred because it is superior in compatibility with polyisobutylene and stability of bisoprolol.

Though the above effect can be attained sufficiently by using a fatty acid alkyl ester alone as an organic liquid ingredient, it is preferable to use a fatty acid alkyl ester in combination with a long-chain alcohol since the permeability and solubility of bisoprolol and the adhesiveness of the adhesive layer to the skin are much more increased. The compounding ratio (A/B) of a fatty acid alkyl ester (A) to a long-chain alcohol (B) is preferably 1:0-1:0.5, more preferably 1:0-1:0.4, and still more preferably 1:0.05-1:0.4, by weight (A/B). When the ratio of the long-chain alcohol (B) is over the above upper limit, it is likely that enhancement of the permeation at high level is hardly maintained as the ratio of the fatty acid alkyl ester (A) is relatively decreased.

As mentioned above, the organic liquid ingredient in many cases works effectively as a permeation enhancer, in which the increased content of the organic liquid ingredient is effective in improvement of transdermal permeability. That is, the organic liquid ingredient contained abundantly in the adhesive layer affords a composition of which the transdermal permeability is increased or can readily be controlled; such a composition as an adhesive may be said ideal for adhesive pharmaceutical preparations. In this connection, the addition of an organic liquid ingredient to the adhesive layer affords an appropriate flexibility and skin adhesiveness to the adhesive layer.

The content of the organic liquid ingredient per the total amount of the adhesive layer is preferably 20 to 40% by weight, more preferably 25 to 38% by weight. When the content of the organic liquid ingredient is less than 20% by weight, the drug possibly exudes from the adhesive layer to form bleeding, which possibly results in decreasing the adhesiveness and making attainment of the sufficient transdermal permeability difficult. When the content of the organic liquid ingredient is over 40% by weight, it is likely that the cohesiveness of the adhesive layer decreases markedly and destruction of cohesion occurs.

The adhesive layer may contain only one kind of polyisobutylene or two or more kinds of polyisobutylenes different in molecular weight.

When only one kind of polyisobutylene is contained, the content of polyisobutylene per the total amount of the adhesive layer is preferably 15 to 60% by weight, more preferably 15 to 55% by weight. When the content of polyisobutylene is less than 15% by weight, it is likely that an inner cohesiveness required for the adhesive layer is hardly attained; on the other hand, when the content is over 60% by weight, it is likely that the skin adhesiveness and tackiness decrease.

When only one kind of polyisobutylene is contained, the viscosity average molecular weight of polyisobutylene is preferably 40,000-5,500,000, more preferably 45,000-5,000,000, though there is no limitation in the molecular weight. When the viscosity average molecular weight is less than 40,000, it is likely that an inner cohesiveness required for the adhesive layer is hardly attained; on the other hand, when it is over 5,500,000, it is likely that the skin adhesiveness and tackiness decrease.

In order to readily cope with both of appropriate cohesiveness in the adhesive layer and appropriate flexibility and skin irritation in the adhesive layer, it is preferable that the adhesive layer contains two or more kinds of polyisobutylenes different in molecular weight. In this specification, the term "two or more kinds of polyisobutylenes different in molecular weight" means those in which the molecular weight distribution peaks exist in two or more independent areas as measured by gel permeation chromatography (GPC). In general, the molecular weight distribution peak of each polyisobutylene is single. Therefore, "two or more kinds of polyisobutylenes different in molecular weight" contain, for example, two or more kinds of polyisobutylenes different in viscosity average molecular weight. As for polyisobutylenes, it is preferable that the polyisobutylenes comprises a first polyisobutylene and a second polyisobutylene of which the molecular weight is relatively lower than that of the first one. The first polyisobutylene may give an appropriate cohesiveness to the adhesive layer; and the second polyisobutylene may give an appropriate flexibility and skin adhesiveness to the adhesive layer.

The molecular weight of the first and second polyisobutylenes are not particularly limited, but in order to secure good adhesiveness and sufficient releasability of bisoprolol, the viscosity average molecular weight of the first polyisobutylene is preferably 1,800,000-5,500,000, more preferably 2,000,000-5,000,000; and that of the second polyisobutylene is preferably 40,000-85,000, more preferably 45,000-65,000. When the viscosity average molecular weight of the first polyisobutylene is less than 1,800,000, it is likely that an inner cohesiveness required for the adhesive layer is hardly attained; on the other hand, when it is over 5,500,000, it is likely that the skin adhesiveness and tackiness decrease. When the viscosity average molecular weight of the second polyisobutylene is less than 40,000, it is likely that a sticky feeling is generated in the adhesive layer to make the skin dirty; on the other hand, when it is over 85,000, it is likely that the skin adhesiveness and tackiness in the adhesive layer decrease. In this connection, the first and second polyisobutylenes respectively can be used in combination of two or more species in the above-mentioned molecular weight ranges.

In this specification, the viscosity average molecular weight means the value which is obtained by calculating a Staudinger's index Jo from the capillary flow time on an Ubbelohde viscometer at 200° C. based on a Suhulz-Blaschke formula and applying the Jo value to the following formulae:

$$Jo = \eta_{SP}/c(1+0.31\eta_{SP})(cm^3/g) \text{ (Suhulz-Blaschke's formula)}$$

$$\eta_{SP} = t/t_o - 1$$

t: flow time of the solution (by Hagenbach-Couette correction formula)
$t_o$ = flow time of the solvent (by Hagenbach-Couette correction formula)
c: the concentration of the solution (g/cm$^3$)
Jo = $3.06 \times 10^{-2}$ MV$^{0.65}$
Mv: viscosity average molecular weight When the adhesive layer comprises two or more kinds of polyisobutylenes different in molecular weight, the total content of polyisobutylenes per the total amount of the adhesive layer is preferably 15 to 60% by weight, more preferably 15 to 55% by weight. When the total amount of polyisobutylene is less than 15% by weight, it is likely that an inner cohesiveness required for the adhesive layer is hardly attained; on the other hand, when it is over 60% by weight, it is likely that the skin adhesiveness and tackiness decrease.

In addition, when the polyisobutylene comprises 2 kinds of polyisobutylenes different in molecular weight, the compounding ratio (C:D) of the first polyisobutylene (C) to the second polyisobutylene (D) is preferably 1:0.1 to 1:3 by weight, more preferably 1:0.1 to 1:2.5, and still more preferably 1:0.3 to 1:2. Among these 2 polyisobutylenes, when the compounding ratio of the second one (D) is over the above upper limit, it is likely that an inner cohesiveness of the adhesive layer is greatly decreased; on the other hand, when it is under the above lower limit, it is likely that the adhesiveness to the skin is greatly decreased.

Tackifier to be used may properly be selected from those known in the field of adhesive pharmaceutical preparations.

Tackifier includes, for example, petroleum resin, terpene resin, rosin resin, cumarone indene resin, styrene resin, styrene-type resin, alicyclic saturated hydrocarbon resin, and the like. In particular, the alicyclic saturated hydrocarbon resin is preferred because preservation stability of the drug is much better. In view of attainment of a good tackiness and cohesiveness, tackifiers having the softening point of 90-150° C., preferably 95-145° C., are preferred. As shown in the invention, the adhesive preparation containing a large amount of an organic liquid ingredient, for example, an alicyclic saturated hydrocarbon resin of which the softening point is lower than 90° C., has a tendency to decrease tackiness and cohesiveness of the adhesive layer. On the other hand, when the softening point is over 150° C., the adhesive layer has a tendency to become hard and decrease adhesiveness to the skin. Accordingly, it is possible to prepare an adhesive preparation having a good skin adhesiveness, cohesiveness and drug stability by properly selecting the kind and softening point of tackifier and adding an organic liquid ingredient in large quantities. In this specification, the softening point means a value determined by a ring and ball method.

The alicyclic saturated hydrocarbon resin includes, for example, commercially available ARKON P-100, ARKON P-115, ARKON P-125, ARKON P-140 (Arakawa Chemical Industries), and the like.

Tackifier may be used alone or in combination of two or more species. When used in combination of two or more species, they may be combined with those different in the kind or softening point of the resins.

The content of tackifier per the total amount of the adhesive layer is preferably 15 to 55% by weight, and more preferably 20 to 50% by weight. When the content of tackifier is less than 15% by weight, the tackiness and cohesiveness become poor in some cases; on the other hand, when it is over 55% by weight, the adhesive layer has a tendency to be hard, decreasing the adhesiveness to the skin.

The adhesive pharmaceutical preparation of the invention comprising the above-mentioned respective ingredients has necessary characteristics required as an adhesive preparation for bisoprolol. Although adjustment of the respective characteristics may be carried out by altering the kind and content of the respective ingredients, other ingredient(s) than the above ones may be added.

For example, in order to further enhance the solubility of the drug in the adhesive layer lowering irritation to the skin favorably, if required, it is possible to add a solubilizing agent comprising a liquid organic ingredient other than the above-mentioned ones to the adhesive layer. Any of the solubilizing agents can be employed as far as they are well compatible with an adhesive, dissolve the drug sufficiently, reduce the possibility of leaking-out of bisoprolol (breeding) from the adhesive ingredient, and have no adverse effect on the adhesiveness and drug-releasing. Specifically, the solubilizing agent includes esters of an organic acid such as fatty acid (e.g., oleic acid, myristic acid, capric acid) or dicarboxylic acid (e.g., adipic acid, sebacic acid) with an alcohol such as ethanol, 2-propanol, and the like; polyhydric alcohol such as glycerin, propylene glycol, and the like, or its di- or tri-ether; esters of polyhydric alcohol with an organic acid such as triacetin; polyethers such as polyethylene glycol, polypropylene glycol, polyoxyethylene hardened castor oil; and others such as crotamiton.

In addition, if required, a proper filler may be added to the adhesive layer in order to improve cohesiveness. Such a filler includes, but is not limited to, inorganic fine particles such as silica, titanium oxide, zinc oxide, magnesium oxide, iron oxide, aluminum hydroxide, talc, kaolin, bentonite, barium sulfate, calcium carbonate, and the like; organic fine particles such as lactose, carbon black, polyvinylpyrrolidone, polyester, polyolefin, polyurethane, polyamide, celluloses, acryl resin, and the like; and fibers such as polyester, polyolefin, polyurethane, polyamide, celluloses, acryl resin, glass, and the like.

In order to improve skin adhesiveness, tackiness, and flexibility, if required, a proper softener may be added to the adhesive layer to give an appropriate skin adhesiveness and tackiness to the adhesive layer. Such a softener includes, but is not limited to, liquid rubber such as liquid polybutene or liquid polyisoprene, in particular, organic liquid ingredient such as liquid hydrocarbon (e.g., liquid paraffin, squalane, squalene), and the like. In addition, if required, a part or all of the surface of the adhesive preparation of the invention may be covered with a cover tape to reinforce the skin adhesiveness and assist the adhesiveness to the skin.

In the invention, when the first polyisobutylene is used in the adhesive layer, it becomes possible to add a large amount of organic liquid ingredient, such that enhancement in permeability of drugs and increase in solubility of drugs may be sufficiently obtained. Thus, it is possible to prepare an adhesive preparation of which decrease of the cohesiveness is inhibited and which leaves no paste on the skin. Moreover, it becomes possible to attain improvement of the skin adhesiveness simultaneously with improvement of the cohesiveness by using a tackifier of which the softening point is much higher within the above-mentioned range of temperature. In this connection, the adhesive layer usually has 30-300 μm in thickness, preferably 60-250 μm.

As for the support, though there is no particular limitation therein, those being substantially impermeable to drugs is preferably used; that is, the support not causing decrease of the content because the active ingredient bisoprolol and additives and the likes are lost from the rear side across the support. The support includes, for example, single layer film such as polyester, nylon, poly(vinylidene chloride), polyethylene, polypropylene, poly(vinyl chloride), ethylene-ethyl acrylate copolymer, polytetrafluoroethylene, ionomer resin, metal foil, and the like, or laminated film thereof. Among these media, in order to enhance the adhesiveness between the support and the adhesive layer (anchorage property), it is preferable to use a laminated film prepared by laminating a non-porous plastic film and a porous film of the above material on a support. In such a case, it is desirous to form the adhesive layer on the side of porous film.

Such a porous film includes those which work to improve an anchorage property to an adhesive layer, specifically including paper, woven fabric, unwoven fabric, knitting cloth, mechanically pored sheet, and the like. Among these films, in view of easiness of handling, paper, woven fabric and unwoven fabric are particularly preferred. The porous film is employed within the range of 10-200 μm in thickness in view of improvement of anchorage property, flexibility of the whole adhesive preparation, and easiness of sticking. In a case of relatively thin adhesive preparation such as plaster type or adhesive tape type, those of 10-100 μm in thickness are employed.

When woven fabric or unwoven fabric is used as a porous film, the basis weight is preferably fixed in 5-30 g/m$^2$, more preferably 6-15 g/m$^2$. The most preferred support is a laminated film prepared from a polyester film of 1.5-6 μm in thickness (preferably polyethylene terephthalate film) and a polyester-made (preferably polyethylene terephthalate-made) unwoven fabric in 6-15 g/m$^2$ as the basis weight.

It is desired that the adhesive surface of the adhesive preparation is laminated with a peel-off liner in order to protect the adhesive surface of the adhesive layer just before use. The peel-off liner, though there is no particular limitation as far as it has a sufficiently light peel-off strength at peel-off, includes, for example, film such as polyester, poly(vinyl chloride), poly(vinylidene chloride), polyethylene terephthalate, and the like, paper such as high quality paper or glassine paper, or film of polyolefin laminated with high quality paper or glassine paper, to which peel-off treatment is made by applying silicone resin or fluororesin on the surface contacting with the adhesive layer. The thickness of the peel-off liner is preferably in 10-200 μm, more preferably 25-100 μm.

As a peel-off liner, a film of polyester (particularly, polyethylene terephthalate) resin is preferably used in view of its barrier effect, its cost and the like. Further, the liner is preferably in 25-100 μm in thickness in view of easiness of handling. The adhesive preparation is used as tape or sheet, though there is no particular limitation in its shape.

The adhesive preparation may be prepared, for example, by dissolving two kinds of polyisobutylenes different in molecular weight, a tackifier, an organic liquid ingredient and bisoprolol in a proper solvent such as toluene, then applying the resulting adhesive solution (composition for forming an adhesive layer, hereinafter the same) on a peel-off liner, drying the same to form an adhesive layer, and then laminating a support on the adhesive layer. Alternatively, for example, the above adhesive solution is directly applied to the support and dried to form an adhesive layer on the support. In this operation, when the adhesive layer is formed by thickly applying an adhesive solution at a time, it becomes difficult to dry evenly in some cases; so, it is appropriate to repeat the applying operation twice or more to give an adhesive layer with sufficient thickness.

It is preferred that the adhesive preparation is preserved or transported in a form of sealed package just before use. Packaging may be made, for example, by packing a single sheet of adhesive preparation or several sheets of piled adhesive preparations with a wrapping material and then tightly closing the periphery with a heat seal. The wrapping material includes, for example, a sheet-form or film-form material, for which there is no particular limitation. In this case, a material allowing heat sealing is desirous in view of easiness of packaging or air-tightness. Such a packaging material includes, specifically and preferably, those using a heat-sealable plastic sheet such as polyethylene, ionomer resin, ethylene-vinyl acetate copolymer, ethylene-vinyl alcohol copolymer, polyacrylonitrile type copolymer, polyvinyl alcohol type copolymer, and the like. In particular, in order to prevent the contamination or oxidation of an active ingredient bisoprolol contained in the adhesive preparation by contact with ambient air, it is preferred to use a laminated gas-impermeable film such as polyester film or metal foil. The packaging material is used in thickness of 10-200 μm. It is more preferable to use a high barrier polyacrylonitrile type copolymer as a lining material in the most inner layer of the above packaging material. Further, it is appropriate to think out a packaging form formed by embossing of the packaging material, dry edge processing (slightly enlarging the above liner portion compared to the adhesive preparation) or blister molding processing (making the contact area small), since it is feared that handling of the package such as taking-out from the package becomes worse when the adhesive ingredient is leaked out from the side of the adhesive preparation.

The adhesive preparation may be taken out from the package, for example by tearing the above package, just before use, and the peel-off liner is peeled off, and the exposed adhesive surface is applied to the skin.

As for the direction for use, the adhesive pharmaceutical preparation containing bisoprolol preferably at a content of 0.1-50 mg, more preferably 1-20 mg, may usually be applied to the skin once a day or every two days for an adult depending on the age of a patient, body weight, condition, and so on.

EXAMPLES

Hereinafter, the invention will be explained specifically by way of Examples, which are not intended to limit the invention. In this connection, the following abbreviation will be used in Examples.
BSP: bisoprolol
B200: Oppanol (R)B200 (BASF) Polyisobutylene,
  Viscosity average molecular weight: 4,000,000
B150: Oppanol (R)B150 (BASF) Polyisobutylene,
  Viscosity average molecular weight: 2,600,000
B12: Oppanol (R)B12 (BASF) Polyisobutylene,
  Viscosity average molecular weight: 55,000
6H: HIMOL6H (Nippon Petrochemicals Co.) Polyisobutylene,
  Viscosity average molecular weight: 60,000
SIS: Clayton D-1107CS (Clayton Polymer Japan) Styrene-isoprene-styrene rubber
P140: ARKON(R)P-140 (Arakawa Chemical Co.) Tackifier
  Alicyclic saturated hydrocarbon resin;
  Softening point: 140° C.
P100: ARKON(R)P-100 (Arakawa Chemical Co.) Tackifier
  Alicyclic saturated hydrocarbon resin;
  Softening point: 100° C.
IPM: CRODAMOL IPM (Croda Japan) isopropyl myristate
DDO: Wako Pure Chemical Ind. 1-dodecanol Examples 1 to 9 and Comparative Examples 1 to 3

A viscous solution of a composition in toluene for forming an adhesive layer was prepared according to the compounding ratio as shown in Table 1, and applied on a liner (75 μm in thickness) made with polyethylene terephthalate (PET) on which silicone peel-off treatment was applied, so that the thickness after drying become 80 μm. This was dried in a drying oven of hot-air circulation type at 100° C. for 5 minutes to yield an adhesive layer. This adhesive layer was stuck together with a laminated film composed of a PET film of 2 μm in thickness and 12 g/m$^2$ PET unwoven fabric on the side of unwoven fabric to yield a sheet-form adhesive preparation. The PET liner on the laminated sheet was peeled off to expose the adhesive surface, on which one or two adhesive layer or layers having the same composition and thickness as above were laminated to yield an adhesive preparation of which the adhesive layer is 160 μm or 240 μm in thickness. The compounding amounts of the respective ingredients as described in Table 1 is indicated by the percentage (% by weight) for the total of the composition for forming the adhesive layer.

Comparative Example 4

A viscous solution of a composition in toluene for forming an adhesive layer was prepared according to the compounding ratio as shown in Comparative Example 4 of Table 1, and applied on a liner (75 μm in thickness) made with polyethylene terephthalate (PET) on which silicone peel-off treatment was applied, so that the thickness after drying become 80 μm.

This was dried in a drying oven of hot-air circulation type at 100° C. for 5 minutes to yield an adhesive layer. This adhesive layer was stuck together with a laminated film composed of a PET film of 2 μm in thickness and 12 g/m² PET unwoven fabric on the side of unwoven fabric to yield a sheet-form adhesive preparation.

Comparative Example 5

Under an inert gas atmosphere, 95 parts by weight of 2-ethylhexyl acrylate, 5 parts by weight of acrylic acid and 0.2 part by weight of benzoyl peroxide were subjected to solution polymerization in ethyl acetate at 60° C. to yield a solution of acryl adhesive. This acryl adhesive (50 parts by weight; solid portion), 40 parts by weight of isopropyl myristate and 10 parts by weight of bisoprolol were mixed homogeneously with stirring in a vessel, to which was added 0.3% by weight (for solid portion of the adhesive) of ethyl acetoacetate aluminum diisopropylate, and the viscosity was adjusted with ethyl acetate. The resulting solution was applied on a liner (75 μm in thickness) made with polyethylene terephthalate (PET) on which silicone peel-off treatment was applied, so that the thickness after drying become 40 μm. This was dried in a drying oven of hot-air circulation type at 100° C. for 5 minutes to yield an adhesive layer. This adhesive layer was stuck together with a laminated film composed of a PET film of 2 μm in thickness and 12 g/m² PET unwoven fabric on the side of unwoven fabric, and then applied to aging at 70° C. for 48 hours to yield a sheet-form adhesive preparation.

The adhesive preparations prepared in Examples 1 to 3 and Comparative Example 5 were tested on transdermal permeability using a piece of the skin removed from the back of a hairless mouse.

<Test Method>

The above adhesive preparation cut into a circular form of 16 mmΦ in diameter was stuck on the horny layer surface removed from the back of a hairless mouse, and the corium side was fit up on a Franz's type diffusion cell and tested using a phosphate buffered physiological saline (pH 7.4) as a receptor solution at 32° C. The receptor solution was sampled at intervals of a certain time, and the content of bisoprolol therein was determined by HPLC to calculate the accumulated amount of permeation for up to 12 hours. After termination of the transdermal permeability test for 12 hours, the adhesive preparation was recovered, and bisoprolol remaining unchanged in the adhesive preparation was extracted with methanol or tetrahydrofuran, and determined by HPLC to calculate the rate of transdermal permeability for 12 hours. From the amount of the remaining bisoprolol, the decreased amount of bisoprolol for 12 hours was calculated and represented by percentage for the initial amount of bisoprolol. Table 2 shows the test results.

TABLE 2

|  | Accumul. amt. of permeation 12 h (μg/cm²) | Rate of dermal migration 12 h (%) |
| --- | --- | --- |
| Example 1 | 220 | 93 |
| Example 2 | 290 | 91 |
| Example 3 | 305 | 94 |
| Comp. Example 5 | 74 | 21 |

In Examples 1 to 3, 90% or more of the drug contained in the adhesive preparation was migrated to the skin, confirming high permeability and high availability. On the other hand, in Comparative Example 5 where an acryl adhesive was used, the permeability was low.

Using the adhesive preparations obtained in Examples 4 to 6 and Comparative Example 1, a skin primary irritation test was performed with a rabbit's skin. The primary irritation test with a rabbit's skin was carried out according to the Draze's method. Table 3 shows the results.

TABLE 1

|  | BSP | Acryl adhesive | SIS adhesive | Polyisobutylene 1st | 2nd | Tackifier | Fatty acid ester | Long chain alcohol | Adhes. layer thick μm | BSP Content (mg/cm²) |
| --- | --- | --- | --- | --- | --- | --- | --- | --- | --- | --- |
| Ex. 1 | 1.4 | — | — | B200 23.3 | 6H 17.8 | P140 27.5 | IPM 30 | — | 160 | 0.25 |
| Ex. 2 | 2 | — | — | B200 23.8 | 6H 18.2 | P140 28 | IPM 23 | DDO 5 | 160 | 0.32 |
| Ex. 3 | 2 | — | — | B200 22.8 | 6H 17.4 | P140 26.8 | IPM 28 | DDO 3 | 160 | 0.32 |
| Ex. 4 | 1.4 | — | — | B150 16.7 | 6H 20.1 | P100 26.8 | IPM 35 | — | 240 | 0.34 |
| Ex. 5 | 1.8 | — | — | B150 19.2 | 6H 27 | P100 27 | IPM 25 | — | 160 | 0.29 |
| Ex. 6 | 1.8 | — | — | B150 18 | 6H 25.1 | P100 25.1 | IPM 30 | — | 160 | 0.29 |
| Ex. 7 | 1.4 | — | — | B200 13.8 | B12 27.4 | P140 27.4 | IPM 30 | — | 160 | 0.23 |
| Ex. 8 | 1.4 | — | — | B200 20.6 | B12 6.8 | P140 41.2 | IPM 30 | — | 160 | 0.23 |
| Ex. 9 | 3 | — | — | B200 18.6 | B12 0 | P140 43.4 | IPM 35 | — | 160 | 0.48 |
| C. Ex. 1 | 0 | — | — | B150 19.7 | 6H 27.4 | P100 27.4 | IPM 25.5 | — | 160 | 0 |
| C. Ex. 2 | 2 | — | — | B150 29.4 | 6H 29.4 | P100 39.2 | — | — | 80 | 0.16 |
| C. Ex. 3 | 2 | — | — | B150 36.5 | 6H 36.5 | — | IPM 25 | — | 80 | 0.16 |
| C. Ex. 4 | 2 | — | 30 | — | — | P100 40 | IPM 28 | — | 80 | 0.16 |
| C. Ex. 5 | 10 | 50 | — | — | — | — | IPM 40 | — | 40 | 0.36 |

TABLE 3

| | P.I.I |
|---|---|
| Example 4 | 0.8 (weak skin irritation) |
| Example 5 | 1.1 (weak skin irritation) |
| Example 6 | 1.5 (weak skin irritation) |
| Comparative Example 1 | 1.5 (weak skin irritation) |

In any adhesive preparations in Examples 4 to 6, P.I.I shows 2 or less, which values are within a category of weak irritants; there is no difference from that of Comparative Example 1 as placebo. Thus, the adhesive preparation of this Example was confirmed to be low in skin irritation.

Using the adhesive preparations obtained in Examples 1 to 9 and Comparative Examples 2 to 4, tackiness feeling, cohesiveness and bleed state were tested. Table 4 shows the results.

<Test Method>
(1) Tackiness Feeling
The peel-off liners of the adhesive preparations obtained in Examples 1 to 9 and Comparative Examples 2 to 4 were peeled off, and then the exposed surface of the adhesive preparations was touched with fingers to evaluate a tackiness according to the following criteria.
o: there are sufficient tackiness, and adhered.
x: No tackiness; insufficient adhesion.
(2) Cohesiveness
The peel-off liners of the adhesive preparations obtained in Examples 1 to 9 and Comparative Examples 2 to 4 were peeled off, and then the exposed surface of the adhesive preparations was touched with fingers to evaluate the cohesiveness of the adhesive layer according to the following criteria.
o: no cobwebbing, no paste remaining observed on a finger.
x: marked cobwebbing, paste remaining observed on a finger.
*: not adhered; the cohesiveness could not be determined.
(3) Bleeding state
The peel-off liners of the adhesive preparations obtained in Examples 1 to 9 and Comparative Examples 2 to 4 were peeled off, and it was judged according to the following criteria whether a liquid material was adhered on the peeled liner.
o: no liquid material was adhered on the peeled liner.
x: liquid material was adhered on the peeled liner.

TABLE 4

| | Tackiness feeling | Cohesiveness | Bleeding |
|---|---|---|---|
| Example 1 | o | o | o |
| Example 2 | o | o | o |
| Example 3 | o | o | o |
| Example 4 | o | o | o |
| Example 5 | o | o | o |
| Example 6 | o | o | o |
| Example 7 | o | o | o |
| Example 8 | o | o | o |
| Example 9 | o | o | o |
| Comp. Ex. 2 | x | * | x |
| Comp. Ex. 3 | x | * | o |
| Comp. Ex. 4 | o | x | o |

From the results shown in Table 4, it was confirmed that the tackiness (adhesiveness) was lost in the absence of an organic liquid ingredient or tackifier. In addition, it was also confirmed that a SIS adhesive has tackiness but is low in cohesiveness; the paste remaining on fingers was confirmed.

Using the adhesive preparations obtained in Examples 1 to 3 and Comparative Example 5, a test for preservation stability was performed. Table 5 shows the results.

<Test Method>
The adhesive preparations obtained in Examples 1 to 3 and Comparative Example 5 were packaged respectively with a PET/A1/HIGH TORON wrapping material (Trade Name, a kind of polyacrylonitril resin), and preserved at 40° C. for 2 months. The content of bisoprolol after termination of the preservation was determined by HPLC, and represented by the percentage of the bisoprolol amount after storage to the amount at the initial stage.

TABLE 5

| | BSP amount after storage (%) |
|---|---|
| Example 1 | 98.9 |
| Example 2 | 99.5 |
| Example 3 | 99.1 |
| Comp. Ex. 5 | 91.6 |

It was confirmed that the adhesive preparations obtained in Examples 1 to 3 had high stability for preservation, but the preparation of Comparative Example 5 using an acryl adhesive showed low stability for preservation.

While the invention has been described in detail and with reference to specific embodiments thereof, it will be apparent to one skilled in the art that various changes and modifications can be made therein without departing from the spirit and scope thereof.

This application is based on Japanese patent application JP 2005-262559, filed on Sep. 9, 2005 and Japanese patent application JP 2006-235270, filed on Aug. 31, 2006, the entire contents of which are hereby incorporated by reference, the same as if set forth at length.

Industrial Applicability

The present invention provides an adhesive pharmaceutical preparation which has a less irritation to the skin surface, keeps excellent stability of bisoprolol in the preparation, and allows continuous administration of a pharmaceutically effective amount of bisoprolol into the living body.

The invention claimed is:

1. An adhesive pharmaceutical preparation containing bisoprolol, which comprises a support and an adhesive layer on one side of the support, wherein the adhesive layer contains bisoprolol, polyisobutylene, a tackifier, and an organic liquid ingredient compatible with polyisobutylene and the tackifier, wherein the content of bisoprolol is 0.5 to 5% by weight, the content of the polvisobutylene is 15 to 60% by weight, the content of the tackifier is 15 to 55% by weight, and the content of the organic liquid ingredient is 20 to 40% by weight.

2. The adhesive pharmaceutical preparation containing bisoprolol as claimed in claim 1, wherein the content of bisoprolol per adhesive area of the adhesive preparation is 0.1 to 1 mg/cm$^2$.

3. The adhesive pharmaceutical preparation containing bisoprolol as claimed in claim 1, which contains a fatty acid alkyl ester as the organic liquid ingredient.

4. The adhesive pharmaceutical preparation containing bisoprolol as claimed in claim 1, which contains a fatty acid alkyl ester and a long chain alcohol as the organic liquid ingredient.

5. The adhesive pharmaceutical preparation containing bisoprolol as claimed in claim 4, wherein the compounding ratio by weight of the fatty acid alkyl ester (A) to the long chain alcohol (B) is 1:0 to 1:0.5 (A:B).

6. The adhesive pharmaceutical preparation containing bisoprolol as claimed in any one of claims 3 to 5, wherein the fatty acid alkyl ester is isopropyl myristate.

7. The adhesive pharmaceutical preparation containing bisoprolol as claimed in claim 1, wherein the polyisobutylene contains two or more kinds of polyisobutylenes different in the molecular weight.

8. The adhesive pharmaceutical preparation containing bisoprolol as claimed in claim 1, wherein the polyisobutylene comprises a first polyisobutylene and a second polyisobutylene having a lower molecular weight than the first polyisobutylene.

9. The adhesive pharmaceutical preparation containing bisoprolol as claimed in claim 8, wherein the viscosity average molecular weight of the first polyisobutylene is 1,800,000- 5,500,000, and the viscosity average molecular weight of the second polyisobutylene is 40,000-85,000.

10. The adhesive pharmaceutical preparation containing bisoprolol as claimed in claim 8 or 9, wherein the compounding ratio by weight of the first polyisobutylene (C) to the second polyisobutylene (D) is 1:0.1 to 1:3 (C:D).

11. The adhesive pharmaceutical preparation containing bisoprolol as claimed in claim 1, wherein the tackifier is an alicyclic saturated hydrocarbon resin.

12. The adhesive pharmaceutical preparation containing bisoprolol as claimed in claim 1, wherein the softening point of the tackifier is 90-150° C.

* * * * *